United States Patent [19]

Miller

[11] 4,369,772

[45] Jan. 25, 1983

[54] METHOD FOR STRENGTHENING A FRACTURED BONE

[75] Inventor: Gary J. Miller, Gainesville, Fla.

[73] Assignee: University of Florida, Gainesville, Fla.

[21] Appl. No.: 144,052

[22] Filed: Apr. 28, 1980

[51] Int. Cl.³ .............................................. A61F 5/04
[52] U.S. Cl. ................................ 128/92 C; 128/92 R; 128/92 G; 128/92 D
[58] Field of Search ............. 128/92 R, 92 BA, 92 D, 128/92 BC, 92 CA, 92 G, 92 C

[56] References Cited

U.S. PATENT DOCUMENTS

| | | | |
|---|---|---|---|
| 2,537,070 | 1/1951 | Longfellow | 128/92 BA |
| 3,255,747 | 6/1966 | Cochran et al. | 128/92 R |
| 3,977,398 | 8/1976 | Burstein | 128/92 BC |
| 4,065,817 | 1/1978 | Branemark et al. | 3/1.91 |
| 4,261,350 | 4/1981 | Branemark et al. | 128/92 BC |
| 4,274,163 | 6/1981 | Malcom et al. | 128/92 C |

*Primary Examiner*—Michael H. Thaler
*Assistant Examiner*—C. W. Shedd
*Attorney, Agent, or Firm*—Arthur G. Yeager

[57] ABSTRACT

Method for strengthening a fractured bone which comprises drilling a hole along the axis of the medullary canal of the bone, inserting into the hole a substantially inflexible tube having an outside diameter less than the diameter of the hole, injecting into the tube and around the tube a semisolid hardenable mixture of methyl methacrylate and poly(methyl methacrylate), and allowing time for the mixture to harden.

6 Claims, No Drawings

METHOD FOR STRENGTHENING A FRACTURED BONE

BACKGROUND OF THE INVENTION

The treatment of bone fractures, resulting from either malignant or benign processes is an important medical procedure. When these fractures are pathological it is necessary to find a means for repairing the fracture and preventing subsequent fractures. If there is sufficient bone stock, methods have been used in the past which include various types of reinforcing nails. More recently there have been instances of supplementing the reinforcement with a hardenable plastic material such as poly (methyl methacrylate). These procedures have involved the use of intramedullary reinforcing nails which are small in diameter and which are then embedded in a hardenable plastic by using hand packing techniques. It has been difficult to fill the necessary voids completely by this method so as to produce a solid supporting structure.

It is an object of this invention to provide an improved process for producing a reinforcement for a fractured bone employing a rigid metallic reinforcement supplemented by a hardenable plastic material capable of filling all the interstices and voids in the bone to provide a solid structure.

BRIEF SUMMARY OF THE INVENTION

This invention provides a method for strengthening a fractured bone which comprises:

a. opening the body to gain access to one end of said fractured bone;

b. drilling a passageway along the axis of the medullary canal of the bone;

c. inserting into said passageway a substantially inflexible tube having an outside diameter less than the diameter of said passageway;

d. injecting into one end of said tube sufficient hardenable semisolid mixture of methyl methacrylate and poly(methyl methacrylate) under superatmospheric pressure to fill the hollow of said tube, the remaining portions of said passageway, and any cavity in said bone intersected by said passageway.

e. allowing time for said mixture to harden; and f. closing said body.

In preferred embodiments of this invention the tube is a metallic tube having an outer surface which is noncircular in cross section, and more preferably, having lengthwise flutes on its outer surface. In another preferred embodiment of this invention the metallic tube is fashioned with a coupling means, e.g. screw threads, at one end thereof to receive a mechanical injector capable of supplying said mixture to the tube under the superatmospheric pressure, normally 10-250 psi.

DETAILED DESCRIPTION OF THE INVENTION

This invention relates to a procedure for the repair of a fractured bone or for the strengthening of a bone which is particulary susceptible to becoming fractured. This invention is especially directed to the treatment of fractured bones or those that might become fractured due to structural compromise caused by disease, by providing an internal reinforcing structure to fill substantially the entire internal void in the bone. The structure which is employed is a central rigid tube which is then embedded in a hardenable plastic material injected into the bone and into the tube so as to fill all of the void spaces inside the bone.

The procedure normally involves a surgical operation to gain access to one end of the bone which is to be strengthened. A hole or passageway is then drilled along the lengthwise axis of the bone through the medullary canal thereof. In the case of a human femur this passageway is about 15-16 mm. in diameter and about 37-38 cm. in length. A tubular rigid reinforcement approximately 11-13 mm. in diameter and 36 cm. in length, curved to fit the normal curvature of the femur, is inserted into the hole and connected to an injection device capable of extruding a hardenable semisolid plastic material into the interior of the tube and around the exterior of the tube so as to fill the entire void in the bone. The injection device is any apparatus suitable for the purpose and capable of supplying the hardenable material under a pressure of about 10-250 psig. Normally such apparatus is a manually operated screw or ratchet device for forcing the semisolid material under pressure through a tubular outlet into the reinforcing tube in the bone. A suitable coupling is employed to join injector to the reinforcement tube, or alternatively, a flexible tube connecting means is employed to join the injector and the reinforcing tube in the bone.

Although other materials may be suitable the desirable and preferred material for injection into the tube and the bone is a polymerizable mixture of methyl methacrylate and poly(methyl methacrylate). Such a mixture must necessarily include suitable reagents to accomplish the hardening in a short period of time. In the case of methyl methacrylate a suitable hardening agent is a peroxide, e.g. benxoyl peroxide. Such a mixture is capable of hardening in a few minutes of time to produce a lightweight solid material providing no undesirable effect on the body of the patient.

The polymerizable mixture may be produced in any of a wide range of viscosities by varying the relative proportions of monomer and polymer in the mixture or by varying the polymer bead size. It is, of course, easier to inject a low viscosity material than a high viscosity material, but at the same time, the higher viscosity material will polymerize to a solid product more readily than will a lower viscosity material. Any of a wide range of viscosities is suitable for the polymerizable plastic reinforcing material in this invention. When a higher viscosity material is employed it may be desirable to have several apertures through the wall of the reinforcing tube at various locations along its length to permit the polymerizable material to be extruded outwardly at those locations to fill the space around the reinforcing tube. If the polymerizable material is of lower viscosity there may be fewer apertures or even no apertures since the viscosity will permit the material to flow out the lower end of the tube and to fill the space around the outside of the tube with little difficulty. With a lower viscosity it is much easier to be assured that all of the voids inside the bone are filled to provide a solid reinforced structure.

As soon as the plastic material has hardened inside the bone and around the reinforcing tube the body of the patient may be closed to its original condition.

In a comparison testing three bones were treated with prior art Kuntscher nails (11×300 mm.) and were supplemented with conventional hand packing around the nails using poly (methyl methacrylate) as a hardenable plastic reinforcement. Three similar bones were reinforced with fluted tubes (11×300 mm.) and packed by means of an injection device described above employing the same plastic reinforcing material as described above in connection with this invention. These two sets of reinforced bones were then tested for resistance to fracture in torsion and it was found that the prior art procedure produced a mean strength value of 57% while the bones reinforced in accordance with the present invention yielded a mean strength value of 102%.

The central reinforcing tube may be made of any substantially inflexible material, stainless steel being preferred. It is important that the outer cross section of the tube be such that it will not twist within the plastic in which it is embedded and this can be accomplished by employing any noncircular cross section. A preferred means for preventing such relative rotation is to employ a tube having a fluted outer surface. With respect to tubes of the size for use in femurs, a typical fluted outer surface would be one having eight equally spaced lengthwise flutes, the outside diameter of the fluted tube being about 12.5 mm. and the root diameter of the outside surface being about 11 mm. If apertures are desirable through the wall of the tube to assist in dispersing the hardenable plastic material to the proper locations these holes may be of any suitable size, e.g. 2-3 mm. in diameter for a tube of the above dimensions. It is obvious that if such apertures are indiscriminately located they might produce weaknesses which would reduce the reinforcing effectiveness of the tube. One method of minimizing the weaknesses produced by such apertures is to arrange them in a spiral configuration from one end to the other end of the tube. When the tube is employed to reinforce a bone having an internal cavity at a known location it is preferable that the apertures be located principally in the location of that cavity so as to be sure to fill the cavity completely with hardenable plastic material.

While the invention has been described with respect to certain specific embodiments, it will be appreciated that many modifications and changes may be made by those skilled in the art, without departing from the spirit of the invention. It is intended, therefore, by the appended claims to cover all such modifications and changes as fall within the true spirit and scope of the invention.

What is claimed as new and what is desired to secure by Letters Patent of the United States is:

1. Method for strengthening a bone which comprises the steps of:
   a. opening the body to gain access to one end of said bone;
   b. drilling a passageway along the axis of the medullary canal of said bone;
   c. inserting into said passageway a substantially elongated inflexible open-ended, hollow, bone-reinforcing, tubular member having an outside diameter less than the diameter of said passageway;
   d. injecting into one end of said tubular member after the inserting step c sufficient hardenable semisolid mixture of methyl methacrylate and poly (methyl methacrylate) under superatmospheric pressure to embed said tubular member in said bone by passage of said mixture from the hollow of said tubular member to fill the remaining portions of said passageway, and to fill any cavity in said bone intersected by said passageway with said hollow remaining filled with said mixture;
   e. allowing sufficient time for said mixture to harden in and around said tubular member; and
   f. closing said body.

2. The method of claim 1 wherein said cavity includes a fracture in said bone which is filled by said mixture.

3. The method of claim 1 further comprising the step of directing said semisolid mixture into said remaining portions of said passageway and into said cavity through lateral openings in said tubular member.

4. The method of claim 1 further comprising the step of directing said semisolid mixture through at least some of the lateral openings in said tubular member which are located adjacent and in general direct alignment to said cavity which cavity extends beyond the limits of said passageway.

5. The method of claim 1 wherein said semisolid mixture is injected into said tubular member under a pressure of 10-250 psig.

6. The method of claim 1 wherein said mixture contains a peroxide catalyst capable of polymerizing said methyl methacrylate.

* * * * *